United States Patent
Kim (10) Patent No.: US 9,427,516 B2
(45) Date of Patent: Aug. 30, 2016

(54) SHOULDER-MOUNTED MULTIFUNCTIONAL HANGING DEVICE HAVING A BODY-FITTING STRUCTURE

(71) Applicant: Mobiu Co., Ltd., Seoul (KR)

(72) Inventor: Hyung-Seok Kim, Seoul (KR)

(73) Assignee: Mobiu Co., Ltd., Seoul (KR)

(*) Notice: Subject to any disclaimer, the term of this patent is extended or adjusted under 35 U.S.C. 154(b) by 265 days.

(21) Appl. No.: 14/239,148

(22) PCT Filed: Oct. 5, 2012

(86) PCT No.: PCT/KR2012/008081
§ 371 (c)(1),
(2) Date: Feb. 17, 2014

(87) PCT Pub. No.: WO2013/051887
PCT Pub. Date: Apr. 11, 2013

(65) Prior Publication Data
US 2014/0217138 A1     Aug. 7, 2014

(30) Foreign Application Priority Data

Oct. 7, 2011   (KR) .................... 10-2011-0102301
Oct. 5, 2012   (KR) .................... 20-2012-0008936 U (51) Int. Cl.
*A61M 5/14*     (2006.01)

(52) U.S. Cl.
CPC .......... *A61M 5/1415* (2013.01); *A61M 5/1417* (2013.01); *A61M 2005/1416* (2013.01); *A61M 2209/082* (2013.01); *A61M 2209/088* (2013.01)

(58) Field of Classification Search
CPC ............... F16M 13/00; F16M 13/04; A61M 2005/1415; A61M 2005/1416; A61M 5/1415; A61M 5/1417; A61M 2209/082; A61M 2209/088

USPC .................. 224/267; 2/459, 461, 45; 602/20
See application file for complete search history.

(56) References Cited

U.S. PATENT DOCUMENTS 2,723,665 A * 11/1955 Goldsmith .......... A61M 5/1415
                                                    128/877
3,090,621 A *  5/1963 Heimers ................... A45F 3/14
                                                    224/200

(Continued)

FOREIGN PATENT DOCUMENTS

JP          2005-246037        9/2005
KR     10-1998-0008250         4/1998

(Continued)

OTHER PUBLICATIONS

International Search Report Dated Mar. 22, 2013 From the Korean Intellectual Property Office Re. PCT/KR2012/008081.

*Primary Examiner* — Corey Skurdal (57) ABSTRACT

The present invention relates to a shoulder-mounted multifunctional hanging device having a structure for fitting onto the body of a user. The shoulder-mounted multifunctional hanging device having a body-fitting structure comprises: a first support unit having a connection portion extending in the lateral direction, and a concave portion contacting the acromion; a second support unit extending from the first support unit and mounted on supraspinatus; and a recess unit that is recessed up to the area in which the first support unit and the second unit are connected. The shoulder-mounted multifunctional hanging device of the present invention is shaped to fit to the structure of the shoulder of a user, and the user may thus be administered an infusion solution in a more comfortable manner without inconvenience to the shoulder.

11 Claims, 8 Drawing Sheets

(56) References Cited

U.S. PATENT DOCUMENTS

| | | | | |
|---|---|---|---|---|
| 3,547,322 | A * | 12/1970 | Dawson | A61M 5/1415 224/148.2 |
| 4,438,763 | A * | 3/1984 | Zablen | A45F 3/14 128/845 |
| 5,626,270 | A * | 5/1997 | Tseng | A61M 5/1415 128/DIG. 6 |
| 5,676,294 | A * | 10/1997 | Eklund | A61M 5/1415 128/DIG. 6 |
| 5,799,846 | A * | 9/1998 | Pfleger | A61M 5/1415 128/DIG. 6 |
| 6,202,214 | B1 * | 3/2001 | Light | A41D 13/0512 2/268 |
| 6,306,111 | B1 * | 10/2001 | Dean | A61F 5/3753 128/DIG. 19 |
| 6,516,981 | B2 * | 2/2003 | Perez | A41D 13/0012 2/102 |
| 7,031,763 | B1 * | 4/2006 | Zhang | A61B 5/055 324/318 |
| 8,944,299 | B2 * | 2/2015 | Siew Kuang Choong | A61M 5/1411 224/148.2 |
| 2012/0228344 | A1 * | 9/2012 | Neoh | A45F 3/14 224/148.4 |

FOREIGN PATENT DOCUMENTS

| | | |
|---|---|---|
| KR | 20-0249139 | 9/2001 |
| KR | 10-2006-0082719 | 7/2006 |
| KR | 20-0429626 | 10/2006 |
| KR | 20-2010-0005802 | 6/2010 |
| WO | WO 98/16270 | 4/1998 |
| WO | WO 2013/051887 | 4/2013 |

* cited by examiner

SHOULDER-MOUNTED MULTIFUNCTIONAL HANGING DEVICE HAVING A BODY-FITTING STRUCTURE

CROSS-REFERENCE TO RELATED APPLICATIONS

This application is a National Phase of PCT Patent Application No. PCT/KR2012/008081 having International filing date of Oct. 5, 2012, which claims the benefit of priority of Korean Patent Application Nos. 10-2011-0102301, filed on Oct. 7, 2011 and 20-2012-0008936, filed on Oct. 5, 2012. The contents of the above applications are all incorporated by reference as if fully set forth herein in their entirety.

TECHNICAL FIELD

The present invention relates to a shoulder-mounted multifunctional hanging device having a body-fitting structure.

BACKGROUND ART

When a user enters a hospital to treat a disease or have an examination, most users get an IV administration from the first day, and a user who has undergone an operation gets an IV administration and a pain-killer injection for reducing pain in an operated portion.

In general, since the users hook an IV or a pain-killer injection to a hook positioned at an upper portion of an IV pole with wheel (IV pole stand with wheel) and moves the IV pole with holding a handle of the IV pole, there is inconvenience in use. Especially, although a patient who has undergone an operation is persuaded into exercising by a doctor, in order for the user who gets the IV administration and the pain-killer injection to go to the restroom or do light exercise in the hospital hallway with holding the IV pole with wheel, since the user needs to move with holding the IV pole with wheel and pushing it by herself or himself, there is inconvenient in use.

In order to solve the above-stated problems, Korean Utility Model Publication No. 2009-0010120 discloses an IV bag shoulder mounting device. However, in the IV bag shoulder mounting device, since an IV Bottle is unstably supported, when a patient walks, there is a problem in that the IV Bottle is shaken.

Further, since wearability of a shoulder hanging device in the supraspinatus muscle, the clavicle, and the acromion may be deteriorated, shoulder pain may be caused.

CITATION LIST

Patent Document Korean Utility Model Publication No. 2009-0010120.

DISCLOSURE

Technical Problem

Accordingly, in order to solve the problems, by providing a shoulder-mounted multifunctional hanging device having a body-fitting structure, when a user gets an IV administration, it is possible to remove some discomfort such as pains in a supraspinatus muscle, the clavicle, and the acromion.

Technical Solution

In order to achieve the object, according to an embodiment of the present invention, there is a provided a shoulder-mounted multifunctional hanging device having a body-fitting structure. The shoulder-mounted multifunctional hanging device includes a first supporting part that is provided with connection parts extending toward side surfaces and is provided with a concave part coming in contact with the acromion; a second supporting part that extends from the first supporting part to be mounted on a supraspinatus muscle; and indented parts that are indented toward portions where the first supporting part and the second supporting part are connected.

Further, the first supporting part may include a first hanging part that is connected to the first supporting part, and a second hanging part that is connected to an end of the first hanging part.

An angle formed by the first hanging part and a top surface of the first supporting part may be an obtuse angle.

Further, the first hanging part may be provided to be relatively rotated with respect to the first supporting part.

The second hanging part may be provided with a container that holds an IV bag. The container may include a first support that is positioned at a lower portion of the second hanging part, provided with a first groove so as to accommodate an IV bag inlet at one side and a second groove so as to accommodate an IV bag outlet at the other side, and supports the IV bag, a second support that is positioned at an intermediate portion of the first support to support the IV bag, and a hook that is provided with at least one or more protrusions positioned at an upper portion of the second hanging part.

A height of the second hanging part may be adjusted at the first hanging part.

Moreover, a buffering part may be provided at a lower portion of at least any one of the first supporting part and the second supporting part.

The second supporting part may have an area in which the second supporting part extends from the first supporting part to be enlarged, and the indented parts may be formed such that as the indented parts are closer to the portions where the first supporting part and the second supporting part are connected, distances between the connection parts of the first supporting part and the second supporting part are decreased, so that the shoulder-mounted multifunctional hanging device is prevented from coming in contact with the clavicle.

An inner surface of the first supporting part may have the same shape as an external shape of the acromion, an inner surface of the second supporting part may have the same shape as an external shape of the supraspinatus muscle, and the clavicle may be positioned at the indented parts.

The indented part may include an arch part formed in the same shape as a protruding external shape of the clavicle.

Further, a band hole may be formed in the second supporting part.

A rotating part at which the hanging part is provided may be provided at an end of the first supporting part.

The connection part may include folding parts that are rotatably provided at ends of the supporting part, and extension parts that extend from the folding parts and are supported by the first supporting part.

Effect of the Invention

According to the present invention, the following effects are obtained.

First, since the device has a shape appropriate for a shoulder structure of a user, the user can more comfortably get an IV administration without being inconvenient.

Second, since the angle formed by the first hanging part and the top surface of the first hanging part is the obtuse angle, a distance between the device and a head of the user is maintained, so that the user can more stably wear the shoulder-mounted multifunctional hanging device.

Third, the shoulder-mounted multifunctional hanging device can hold an IV bag as well as an IV Bottle and can adjust a height of the hanging part, so that the shoulder-mounted multifunctional hanging device can be widely used.

Fourth, since the first hanging part can be rotated, the hanging part is rotated toward the front side of the user to use a device such as a smart phone mounted on a mounted part, so that it is possible to improve convenience of the user.

Fifth, since the first hanging part and the second hanging part are used to adjust a height, it is possible to adjust the shoulder-mounted multifunctional hanging device to be appropriate from a body shape of the user.

Sixth, the user can more comfortably wear the shoulder-mounted multifunctional hanging device by providing the buffering part.

Seventh, since the indented parts are formed so as not to affect the clavicle, the user can more comfortably wear the shoulder-mounted multifunctional hanging device.

Eighth, since the shoulder-mounted multifunctional hanging device can hold the IV Bottle stably and conveniently while the user moves, the user can more comfortably get treatment.

Ninth, since the shoulder-mounted multifunctional hanging device includes the folding parts, the shoulder-mounted multifunctional hanging device can be more compactly stored.

Tenth, since the rotating part can be rotated, the user adjusts the shoulder-mounted multifunctional hanging device in a desired direction, so that the user can use the shoulder-mounted multifunctional hanging device at the most appropriate position.

BEST MODE

Figure 1:
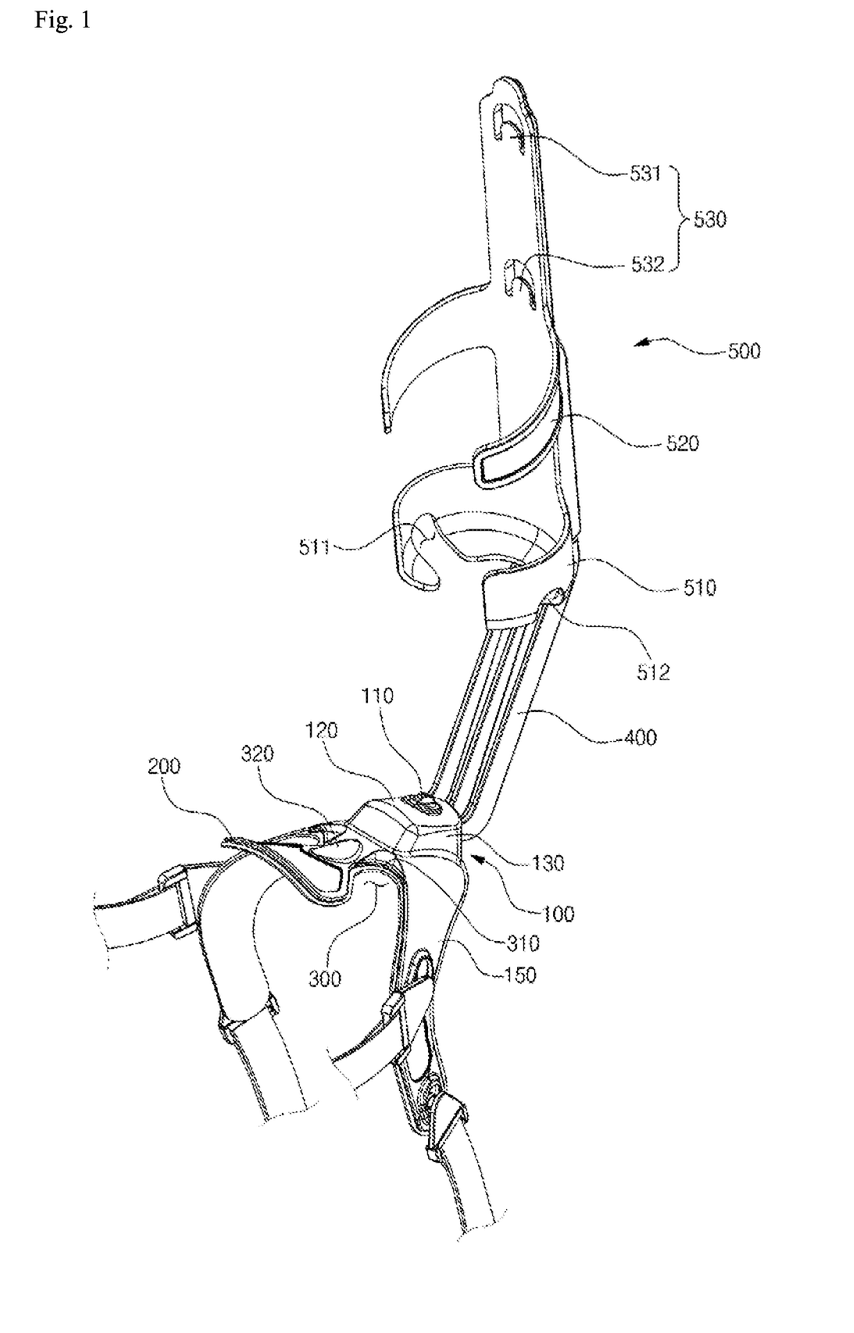
FIG. 1 is an entire perspective view of a shoulder-mounted multifunctional hanging device according to a preferred embodiment of the present invention.
Figure 3:
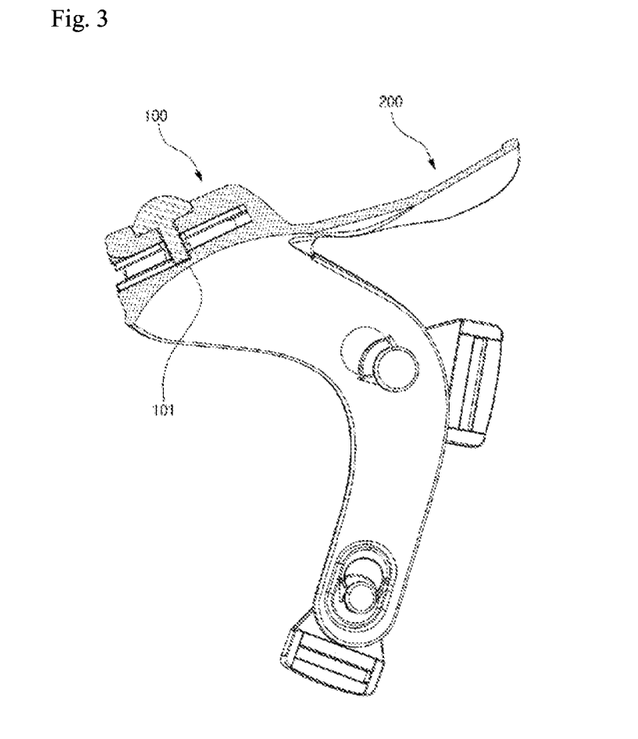
FIG. 3 is a cross-sectional view of a first supporting part according to the preferred embodiment of the present invention.

FIG. 1 is an entire perspective view of a shoulder-mounted multifunctional hanging device having a body-fitting structure according to a preferred embodiment of the present invention, and FIG. 3 is a cross-sectional view of a first supporting part 100 according to the preferred embodiment of the present invention.

The first supporting part 100 is mounted on the acromion, and has a concave part 101 that is concave inwards.

Connection parts 150 are formed to respectively extend from the left and the right of the first supporting part 100.

A second supporting part 200 extends from the first supporting part 100 to be mounted on a supraspinatus muscle.

The second supporting part 200 has a second surface 332 in which as the second surface is far away from the first supporting part 100, an area thereof is increased.

First surfaces 331 are respectively formed at upper edges in a longitudinal direction of the connection parts 150.

Indented parts 300 are respectively formed between the first surfaces 331 and the second surface 332, and convex parts 310 that extend from the first supporting part 100 in a convex shape are formed at the indented parts.

The indented parts 300 allow the clavicle of a user to naturally pass, and the convex parts 310 surround the clavicle of the user to allow the user to comfortably wear the device.

The inside of the first supporting part 100 has a concave shape so as to be appropriate for the acromion, and, thus, the user can wear the device more stably and comfortably.

The second supporting part 200 is a part mounted on the supraspinatus muscle, and serves to more stably support the shoulder-mounted multifunctional hanging device having a body-fitting structure (hereinafter, referred to as a shoulder hanging device). Further, the second supporting part has a shape appropriate for a shape of the supraspinatus muscle to allow the user to wear the device stably and comfortably.

A reinforcing part 320 that is convex upwards is formed at a position where the second supporting part 200 is connected to the first supporting part 100, so that the second supporting part 200 can more stably support the shoulder hanging device.

A first hanging part 400 is provided at a fixing part 130 where the connection parts 150 are connected to the first supporting part 100.

A second hanging part 500 is provided at an upper side of the first hanging part 400.

The first hanging part 400 is inserted into the fixing part 130 of the first supporting part 100 to be fixed by a first fixing screw 110.

The first hanging part 400 extends upwards while forming an obtuse angle with respect to a top surface of the first supporting part 100 to be coupled to the second hanging part 500.

A first container 510 is formed at a lower portion of the second hanging part 500 so as to hold an IV Bottle, and s second container 520 is formed at an intermediate portion thereof.

The first container 510 is provided with a support 513 so as not to fall the IV Bottle downwards, and the support 513 is provided with a first groove 511 and a second groove 512 so as to accommodate an IV bag having a rectangular shape.

Preferably, the first groove 511 and the second groove 512 are symmetric with each other.

Since the support 513 is provided with the first groove 511 and the second groove 512, the rectangular shape of the IV bag can be maintained, so that an IV bag inlet or an IV bag outlet formed in the IV bag is accommodated in the first groove 511 or the second groove 512. Thus, the IV bag can be maintained in a vertical direction, so that the user can more stably get an IV.

More specifically, an IV back inlet into which the IV is additionally injected and an IV back outlet from which the IV is discharged are formed at a lower portion of the IV bag having the rectangular shape. Since the IV bag is made of transparent soft resin, when the IV bag inlet or the IV bag outlet is crushed at the lower portion of the IV bag, it is difficult for the IV to move. The first groove 511 and the second groove 512 are formed so as to prevent the lower portion of the IV bag from being crushed due to interference of the support 513.

Since the second container 520 is positioned above the first container 510 and has a shape in which the second container extends toward the left and the right from the second hanging part to be rounded and both ends thereof are open, the IV Bottle is allowed to move through the opening, so that the IV Bottle is comfortably held.

More specifically, when a side portion of the IV Bottle is pulled toward the opening of the second container 520 while the IV Bottle is mounted on the support 513, the second container 520 is slightly open in a left and right direction to allow the IV Bottle to pass, and is then returned in an original state to allow the IV Bottle supported by the support 513 to be fixed.

At least one or more protrusions having different heights are formed at an upper portion of the second hanging part 500 to hang various kinds of IV bags.

Preferably, a first protrusion 531 is formed to protrude from an upper end of the second hanging part 500 to hang an IV bag of 1000 cc or more, and a second protrusion 532 is formed to protrude from an intermediate portion of the second hanging part 500 to hang an IV bag of 500 cc.

Since the second handing part 500 is provided with the first container 510, the second container 520, and a hook 530, it is possible to more stably support the IV Bottle or the IV bag without being shaken with the movement of the user when the user walks.

The connection part 150 includes a horizontal connection part 151 that diagonally extends from the acromion of the user toward the chest, and a vertical connection part 152 that is formed to be inclined under the arm of the user from the horizontal connection part 151.

The vertical connection part 152 is preferably formed to be inclined under the arm of the user so as to minimize interference with the movement of the arm of the user when the user wears the shoulder hanging device.

The horizontal connection part 151 is provided with a second detaching part 711 to allow a second band 700 that surrounds the chest of the user to be detached.

The vertical connection part 152 is provided with a first detaching part 611 disposed under the second detaching part 711 to allow a first band 600 that surrounds under the arm of the user to be detached.

The first band 600 is provided with a first clamping part 610 capable of adjusting a length of the band to be appropriate for a body shape of the user.

The second band 700 is provided with a second clamping part 710 capable of adjusting the length of the band to be appropriate for the body shape of the user.

A buffering part 800 is preferably attached to the inside of the shoulder hanging device while having a shape corresponding to the shoulder hanging device.

The buffering part 800 may be formed so as to be detachably attached to the shoulder hanging device, and may be preferably made of a material that can absorb the impact and has a good ventilation property.

Figure 2:
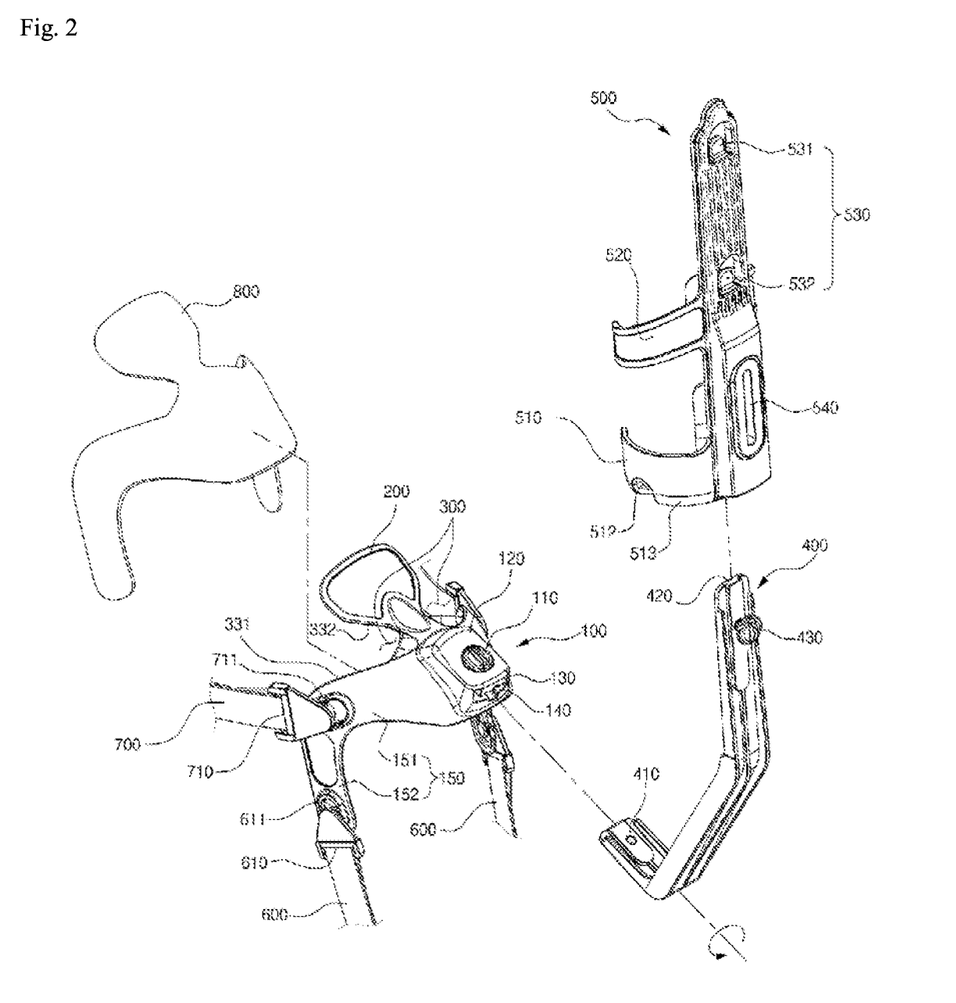
FIG. 2 is an exploded perspective view of the shoulder-mounted multifunctional hanging device according to the preferred embodiment of the present invention.

The first supporting part 100 is provided with a polygonal groove 140 at the fixing part 130.

A first coupling part 410 of the first hanging part 400 has a shape corresponding to the polygonal groove 140 to be inserted into the polygonal groove 140.

By inserting the first coupling part 410 into the polygonal groove 140 and by coupling the first fixing screw 110 provided at the top surface of the first supporting part 100 to a screw groove formed at the first coupling part 410, the first hanging part 400 is fixed to the first supporting part 100.

A second coupling part 420 is formed at an upper portion of the first hanging part 400, and a second fixing screw 430 is formed at the second coupling part 420.

The second coupling part 420 is inserted into a second fastening part 540 formed at the second hanging part 500 to be fixed by the second fixing screw 430.

The second fastening part 540 is formed such that a height thereof is adjusted at the second coupling part 420.

Figure 4:
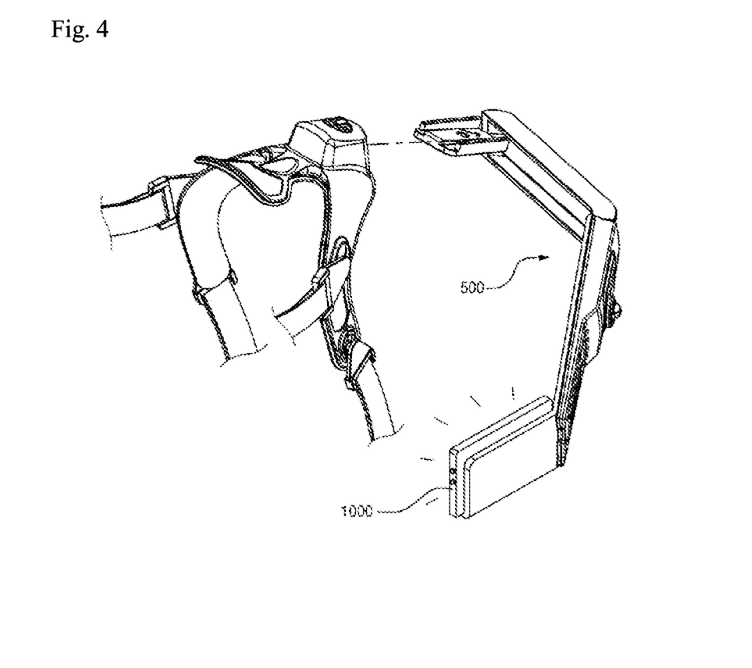
FIG. 4 is a perspective view of a shoulder-mounted multifunctional hanging device according to a second preferred embodiment of the present invention.

FIG. 4 is a perspective view of a shoulder hanging device according to a second preferred embodiment of the present invention.

The first hanging part 400 may be formed to be rotated around the first coupling part 410 as shown in FIG. 2, and the user can mount a peripheral device 1000 such as a smart phone, a tablet PC, or a MP3 player on the second hanging part 500 to use the peripheral device 1000 in front of eyes of the user.

When the user wears the shoulder hanging device on a left shoulder, the user can use the peripheral device 1000 while viewing the peripheral device in front of eyes of the user as shown in FIG. 4.

Further, the shoulder hanging device has a symmetric shape back and forth, and can be used for both a right shoulder and a left shoulder of the user.

Next, still another preferred embodiment of the present invention will be described in detail with reference to the accompanying drawings.

Figure 5:
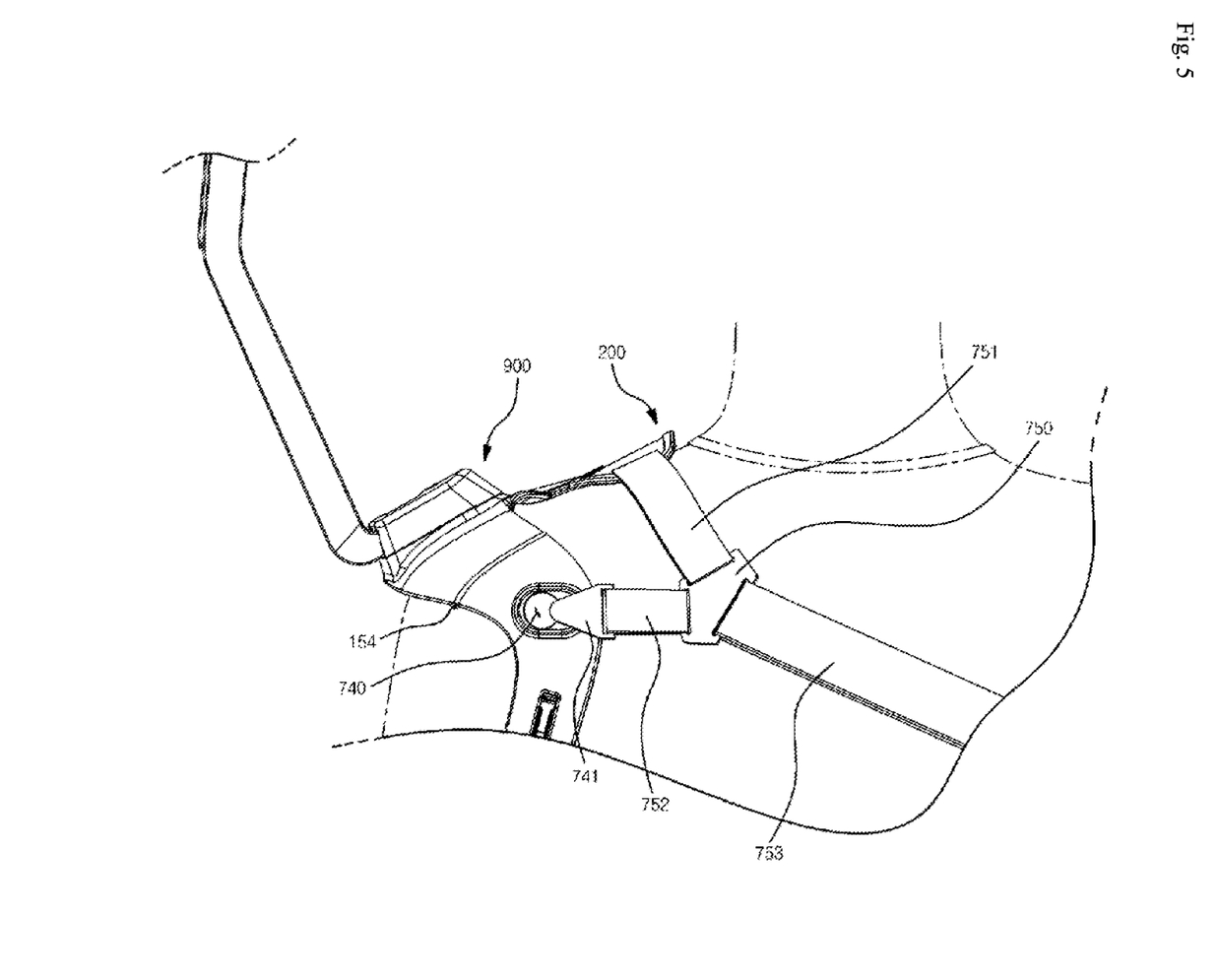
FIG. 5 shows a state where a user wears a shoulder-mounted multifunctional hanging device according to a third preferred embodiment of the present invention.
Figure 6:
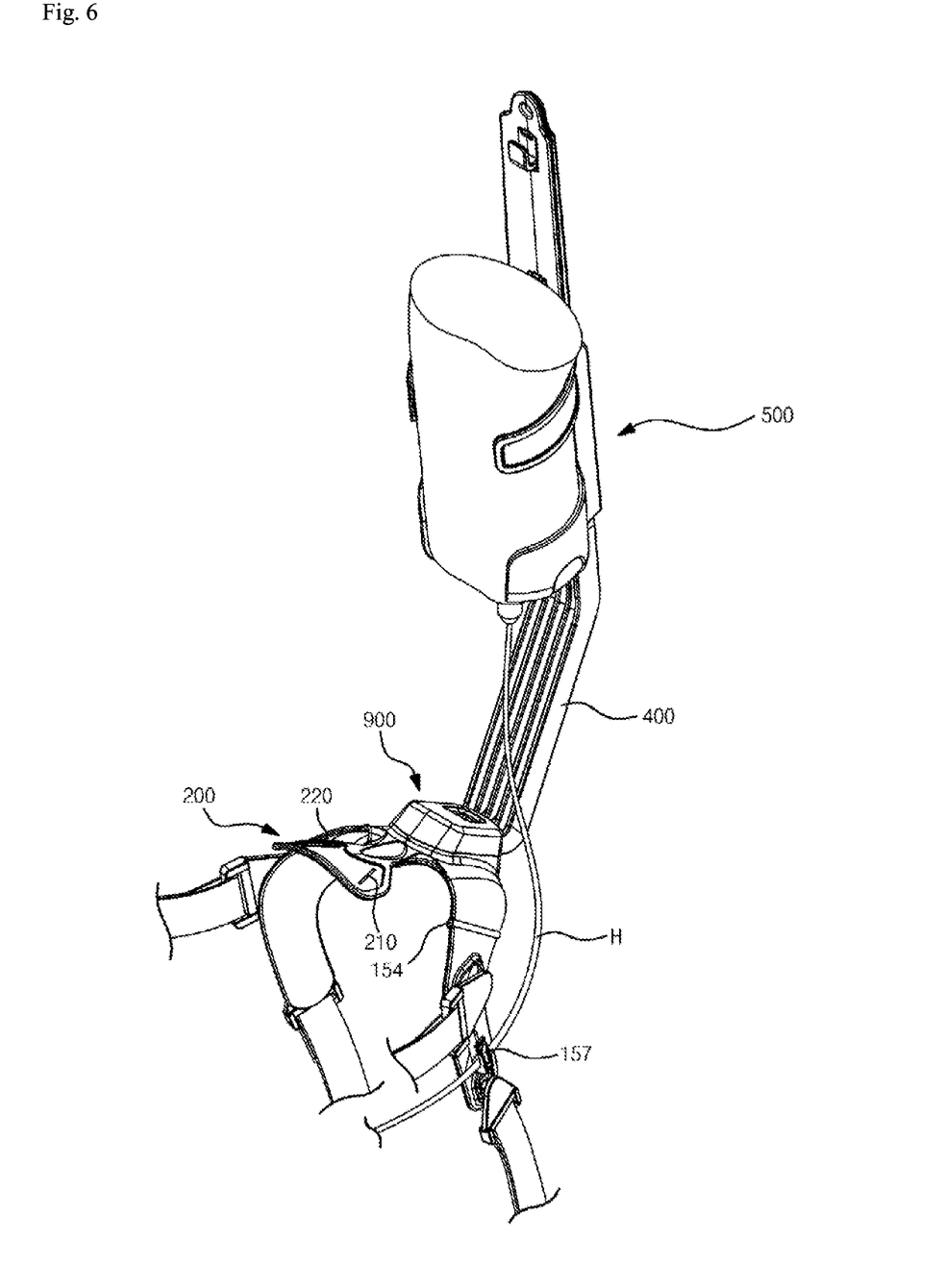
FIG. 6 is a perspective view of the shoulder-mounted multifunctional hanging device according to the third preferred embodiment of the present invention.

FIG. 5 is a diagram showing a state where the user wears a shoulder hanging device according to a third preferred embodiment of the present invention, and FIG. 6 is a perspective view of the shoulder hanging device according to the third preferred embodiment of the present invention.

A second hanging part 500 is provided at an upper side of a first hanging part 400.

A first insertion part 403 fastened to a rotating part 900 is formed at a lower side of the first hanging part 400, and a second insertion part 401 fastened to the second hanging part 500 is formed at the upper side of the first hanging part 400.

A button 405 is formed at a lower side of the second insertion part 401 of the first hanging part 400, and the button 405 is formed to be detachably attached to the second fastening part 504 formed at the second hanging part 500.

Since a button is formed at a top surface of the first insertion part 403, the first insertion part 403 can be detachably attached to the rotating part 900 by the button.

Figure 7:
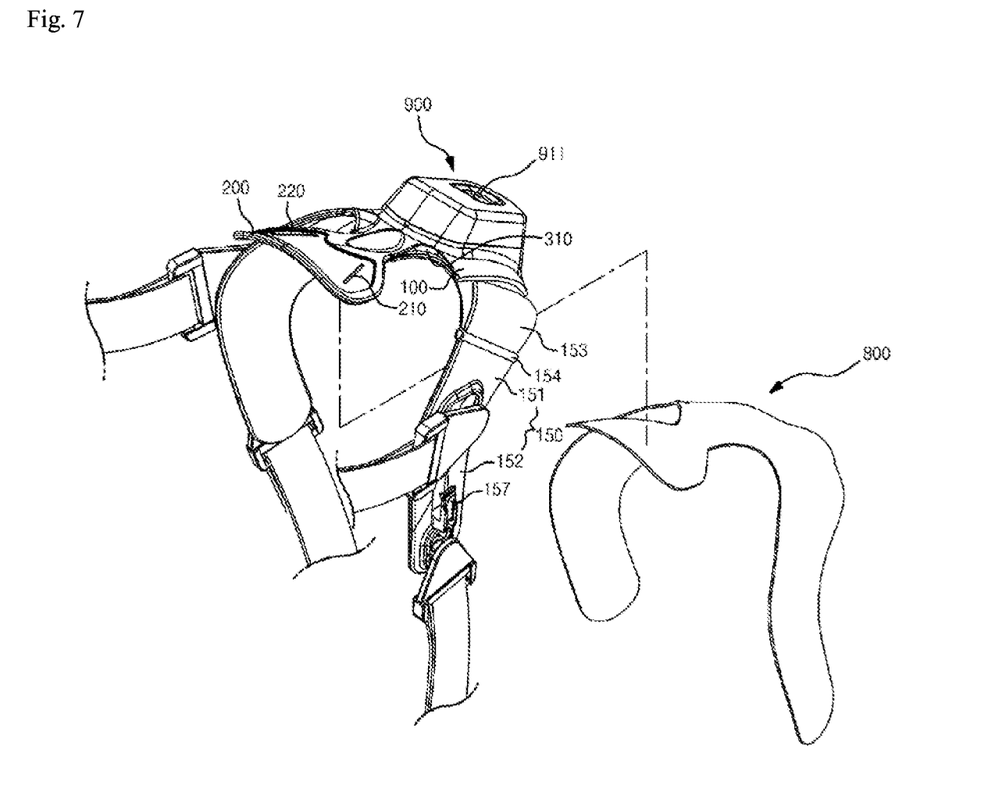
FIG. 7 is an exploded perspective view of a buffering part according to the third preferred embodiment of the present invention.

FIG. 7 is an exploded perspective view of a buffering part 800 according to the third preferred embodiment of the present invention.

The shoulder hanging device in the present invention can be selectively used for the right shoulder or the left shoulder of the user.

Referring to FIG. 6, a first band hole 210 that is open in an elongated shape is formed at a right side of a second supporting part 200, and a second band hole 220 that is open in an elongated shape is formed at a left side of the second supporting part 200.

One side of a first connection band 751 is connected to the second band hole 220 and the other side thereof is connected to a connector 750.

One side of a second connection band 752 is connected to a detaching plate 741 and the other side thereof is connected to the connector 750.

One side of a third connection band 753 is connected to the connector 750, and the third connection band is wound around the back of the user toward the front side of the user while surrounding the back of the user.

The detaching plate 741 can be detachably attached to a detaching groove 740, and a folding part 154 is formed at an upper side of the detaching groove 740.

The rotating part 900 is provided to be rotated at an upper side of the shoulder hanging part.

Referring to FIG. 7, the buffering part 800 has a shape corresponding to the shoulder hanging device to be detachably attached to the inside of the shoulder hanging device.

The buffering part 800 may be preferably made of a material that can absorb the impact and has a good ventilation property.

Figure 8:
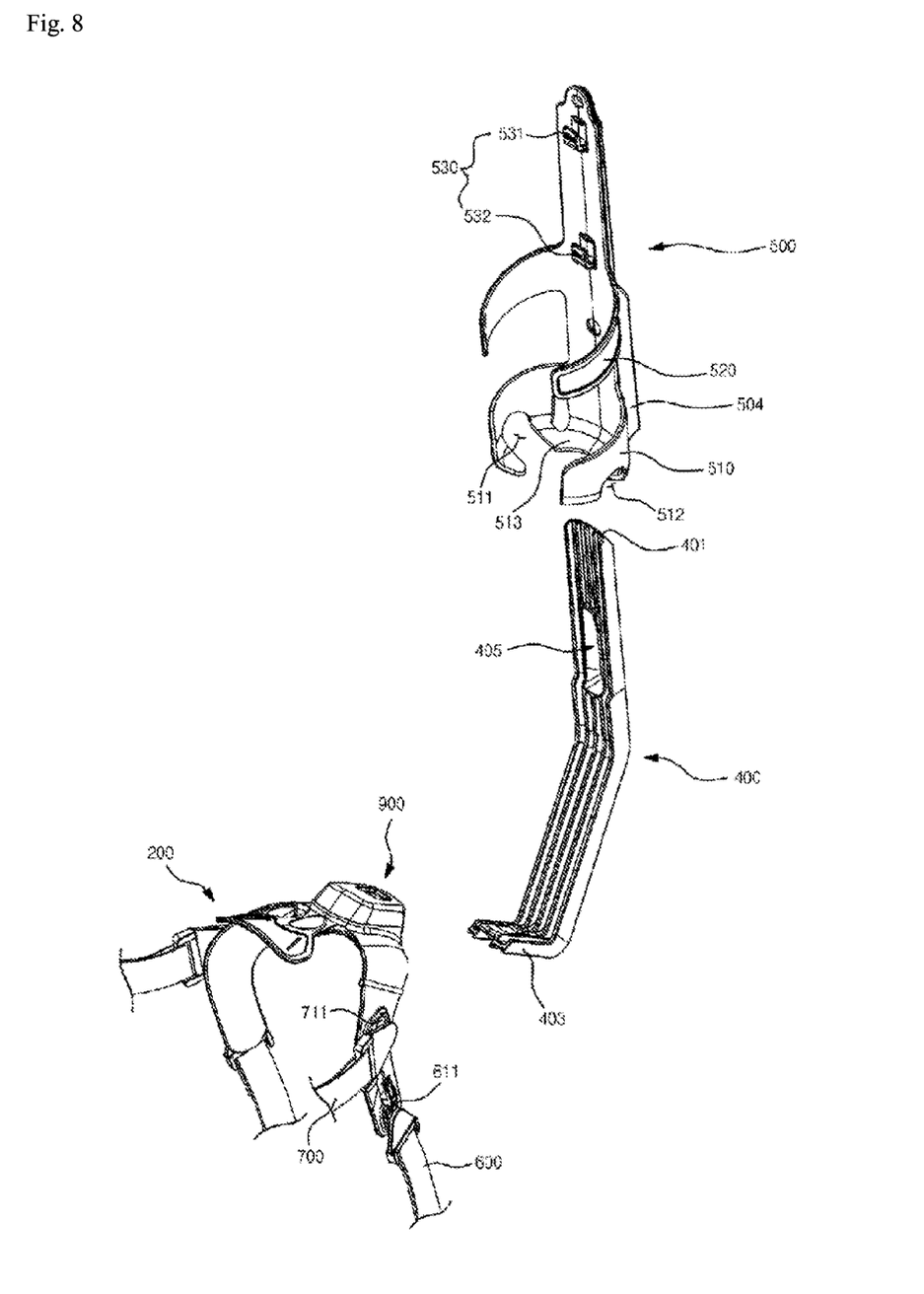
FIG. 8 is an exploded perspective view of the shoulder-mounted multifunctional hanging device according to the third preferred embodiment of the present invention.

FIG. 8 is an exploded perspective view of the shoulder hanging device according to the third preferred embodiment of the present invention.

Since an IV tube hook 157 formed at a connection part 150 guides a tube H, the tube H is prevented from being twisted.

A hook 530 is formed at the second hanging part 500 so as to hook the IV Bottle.

Figure 9:
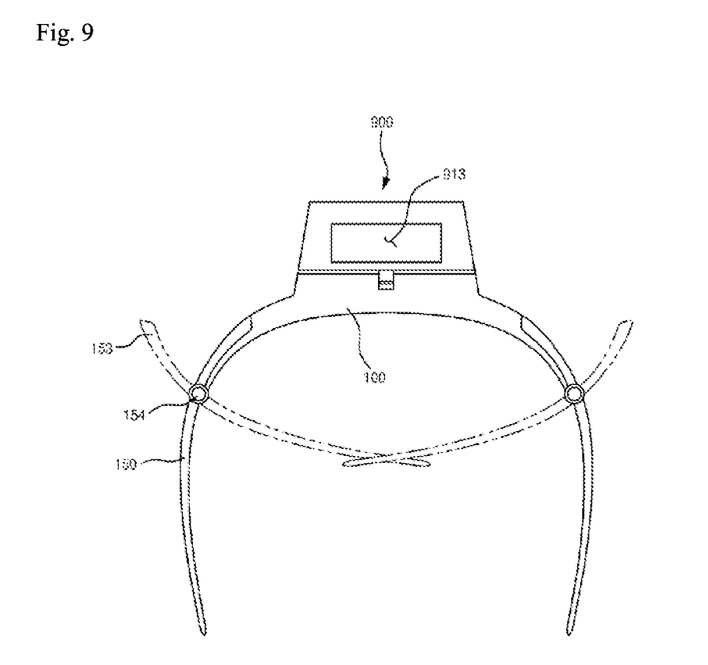
FIG. 9 is an operation diagram of a folding part according to the third preferred embodiment of the present invention.

FIG. 9 is an operation diagram of the folding part 154 according to the third preferred embodiment of the present invention.

The folding parts 154 are respectively formed at the connection parts 150 and 150.

The folding parts 154 are connected to the first supporting part 100 to be rotated.

The connection part 150 has an extension part 153 that extends to pass through the folding part 154.

When the folding parts 154 are rotated to be folded as shown in FIG. 9, the extension parts 153 are separated from the first supporting part 100.

Meanwhile, when the user uses the shoulder hanging device, since the extension parts 153 are supported by the first supporting part 100, the shoulder hanging device can be stably used.

When the user stores the shoulder hanging device, the user can more compactly store the shoulder hanging device by folding the connection parts 150 by using the folding parts 154 as a reference.

Figure 10:
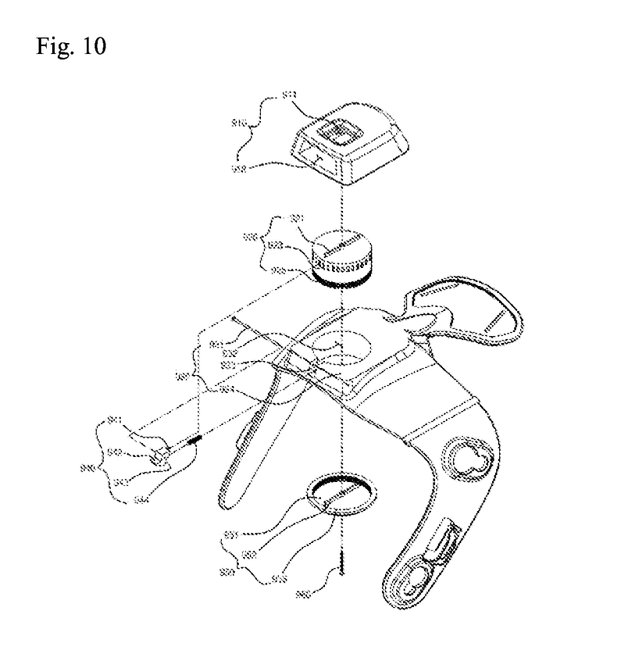
FIG. 10 is an exploded perspective view of a rotating part according to the third preferred embodiment of the present invention.

FIG. 10 is an exploded perspective view showing a configuration of the rotating part 900 according to the third preferred embodiment of the present invention.

The rotating part 900 includes an upper cap 910, an insertion member 920 inserted into the upper cap 910, a base part 930 on which the insertion member 920 and the upper cap 910 is mounted, and a lower cap 950 that connects the insertion member 920 and the upper cap 910 to allow the insertion member and the upper cap to be rotated at the base part 930 so as not to be separated from each other.

An inlet 913 is formed at a side surface of the upper cap 910 so as to allow the first insertion part of the first hanging part to be inserted.

A button groove 911 is formed at an upper end of the upper cap 910.

The button formed at the upper end of the first insertion part of the first hanging part is fastened to the button groove 911.

The insertion member 920 has a bottom part 925, and the entire shape of the insertion member is a cylindrical shape.

First protrusions 921 are formed in an elongated shape at an upper end of the insertion member 920 with respect to a central axis.

The first protrusions 921 are inserted into a groove (not shown) formed on a bottom surface of the upper cap 910 to allow the insertion member 920 to be coupled to the bottom surface of the upper cap 910 while being firmly supported by the bottom surface thereof.

A plurality of fixing grooves 923 is formed at the upper side surface of the insertion member 920 along a circumferential surface.

A first settling surface 934 is formed at the base part 930 around an accommodation part 932, and a stepped portion 933 and a pin 931 are provided at the base part.

More specifically, the base part 930 has a hollow accommodation part 932 formed in a round shape so as to accommodate the insertion member 920.

The first settling surface 934 is a flat surface formed along an edge of the accommodation part 932, and the upper cap 910 is mounted on the first settling surface.

A hole having a diameter corresponding to that of the pin 931 is formed in a front side surface of the base part 930 so as to allow the pin 931 to be inserted.

The stepped portion 933 is formed at an intermediate portion of the front side surface of the base part 930.

A lever 940 is provided with a hole penetrating a left surface and a right surface thereof to accommodate the pin 931 provided at the base part 930.

The lever 940 has a handle 942 protruding toward the left side of the drawing, and has a supporting surface 943 vertically extending from the handle 942.

The lever 940 has a fixing protrusion 941 protruding toward a right side from an upper end of the supporting surface 943.

The lever 940 is coupled to the stepped portion 933 formed at the base part 930 by the pin 931.

After penetrating a front left surface of the base part 930, the pin 931 passes through the hole formed in the lever 940, and then penetrates a front right surface of the base part 930.

Since a spring 944 is provided between the stepped portion 933 and the supporting surface 943 of the lever 940, the fixing protrusion 941 of the lever 940 constantly applies force toward the fixing groove 923 of the insertion member 920.

The lower cap 950 has a second settling surface 951 so as to accommodate the bottom surface 925 of the insertion member 920.

A second protrusion 952 having the same shape as the first protrusion 921 formed at the aforementioned insertion member 920 is formed at an upper portion of the second settling surface 951.

The second protrusion 952 is fixed onto the groove (not shown) formed at the bottom surface 925 of the insertion member 920.

A flange 953 extends from an edge of the second settling surface 951 and has a diameter greater than that of the accommodation hole of the base part 930.

In other words, the lower cap 950 is fastened to the upper cap 910 at which the insertion member 920 is provided by the screw 960 so as to allow the upper cap 910 to be rotated at the base part 930 not to be separated therefrom.

Next, an operation in which the user rotates the rotating part 900 will be described.

When the user pushes down the handle 942 of the lever 940, the fixing protrusion 941 is separated from the fixing groove 923 while the lever 940 is rotated around the pin 931 to rotate the rotating part 900.

When the user quits the handle 942 of the lever 940 while the rotating part 900 is rotated, the lever 940 is rotated around the pin 931 by the spring 944, and the fixing protrusion 941 is inserted into the fixing groove 923.

The rotating part 900 can be fixed so as not to be rotated by fastening the fixing protrusion 941 to the fixing groove 923.

The present invention is not limited to the embodiments of the present invention in view of the object and the technical spirit thereof. It is to be appreciated that technologies that can be easily invented from the present invention are incorporated in the scope of the present invention. A change of commercial design, a change in shape, a change in quality, an increase in the number of components and a change of color in technologies equivalent to or subordinate to the present invention would not be mentioned.

DESCRIPTION OF MAIN REFERENCE NUMERALS OF DRAWINGS

100: First supporting part, 101: Concave part
110: First fixing screw, 120: Top surface
130: Fixing part, 140: Polygonal groove
150: Connection part, 153: Extension part
154: Folding part, 157: IV tube hook
151: Horizontal connection part, 152: Vertical connection part
200: Second supporting part, 210: First band hole
220: Second band hole, 300: Indented part
310: Convex part, 331: First surface
332: Second surface, 400: First hanging part
401: Second insertion part, 403: First insertion part
405: Button, 500: Second hanging part
510: First container, 511: First groove
512: Second groove, 513: Support
520: Second container, 530: Hook
531: First protrusion, 532: Second protrusion
540: Second fastening part, 600: First band
610: First clamping part, 611: First detaching part
700: Second band, 710: Second clamping part
711: Second detaching part, 740: Detaching groove
711: Detaching plate, 750: Connector
751: First connection band, 752: Second connection band
753: Third connection band, 800: Buffering part
900: Rotating part, 1000: Peripheral device

The invention claimed is:

1. A shoulder-mounted multifunctional hanging device having a body-fitting structure, comprising:
  a first supporting part that is provided with connection parts extending toward side surfaces and is provided with a concave part coming in contact with the acromion;
  a second supporting part that extends from the first supporting part to be mounted on a supraspinatus muscle; and
  indented parts that are indented toward portions where the first supporting part and the second supporting part are connected,
  wherein the first supporting part includes:
  a first hanging part that is connected to the first supporting part; and
  a second hanging part that is connected to an end of the first hanging part,
  wherein the second hanging part is provided with a container that holds an IV bag, and
  wherein the container includes:
  a first support that is positioned at a lower portion of the second hanging part, provided with a first groove so as to accommodate an IV back inlet at one side and a second groove so as to accommodate an IV bag outlet at the other side, and supports the IV bag;
  a second support that is positioned at an intermediate portion of the first support to support the IV bag; and
  a hook that is provided with at least one or more protrusions positioned at an upper portion of the second hanging part.

2. The shoulder-mounted multifunctional hanging device having a body-fitting structure according to claim 1, wherein an angle formed by the first hanging part and a top surface of the first supporting part is an obtuse angle.

3. The shoulder-mounted multifunctional hanging device having a body-fitting structure according to claim 1, wherein the first hanging part is provided to be relatively rotated with respect to the first supporting part.

4. The shoulder-mounted multifunctional hanging device having a body-fitting structure according to claim 1, wherein a height of the second hanging part is adjusted at the first hanging part.

5. The shoulder-mounted multifunctional hanging device having a body-fitting structure according to claim 1, wherein a buffering part is provided at a lower portion of at least any one of the first supporting part and the second supporting part.

6. The shoulder-mounted multifunctional hanging device having a body-fitting structure according to claim 1,
  wherein the second supporting part has an area in which the second supporting part extends from the first supporting part to be enlarged, and
  the indented parts are formed such that as the indented parts are closer to the portions where the first supporting part and the second supporting part are connected, distances between the connection parts of the first supporting part and the second supporting part are decreased, so that the shoulder-mounted multifunctional hanging device is prevented from coming in contact with a clavicle.

7. The shoulder-mounted multifunctional hanging device having a body-fitting structure according to claim 1,
  wherein an inner surface of the first supporting part has the same shape as an external shape of the acromion, an inner surface of the second supporting part has the same shape as an external shape of the supraspinatus muscle, and a clavicle is positioned at the indented parts.

8. The shoulder-mounted multifunctional hanging device having a body-fitting structure according to claim 1, wherein the indented part includes an arch part formed in the same shape as a protruding external shape of a clavicle.

9. The shoulder-mounted multifunctional hanging device having a body-fitting structure according to claim 1, wherein a band hole is formed in the second supporting part.

10. The shoulder-mounted multifunctional hanging device having a body-fitting structure according to claim 1, wherein a rotating part at which the first hanging part is provided is provided at an end of the first supporting part.

11. The shoulder-mounted multifunctional hanging device having a body-fitting structure according to claim 1,
   wherein the connection part of the first supporting part includes:
   folding parts that are rotatably provided at ends of the first supporting part; and
   extension parts that extend from the folding parts and are supported by the first supporting part.

\* \* \* \* \*